US00PP25460P2

(12) United States Plant Patent
Moore

(10) Patent No.: US PP25,460 P2
(45) Date of Patent: Apr. 21, 2015

(54) ***LYCHNIS* PLANT NAMED 'PMOORE05'**

(50) Latin Name: *Lychnis×arkwrightii*
Varietal Denomination: Pmoore05

(71) Applicant: Peter R. Moore, Stockbridge (GB)

(72) Inventor: Peter R. Moore, Stockbridge (GB)

( * ) Notice: Subject to any disclaimer, the term of this patent is extended or adjusted under 35 U.S.C. 154(b) by 15 days.

(21) Appl. No.: 13/986,338

(22) Filed: Apr. 22, 2013

(51) Int. Cl.
*A01H 5/00* (2006.01)

(52) U.S. Cl.
USPC ..... Plt./452

(58) Field of Classification Search
USPC ..... Plt./452
See application file for complete search history.

*Primary Examiner* — Susan McCormick Ewoldt
*Assistant Examiner* — Keith Robinson
(74) *Attorney, Agent, or Firm* — Penny J. Aguirre

(57) ABSTRACT

A new cultivar of *Lychnis*, 'Pmoore05', that is characterized by its strong growth habit with a quicker time to produce a marketable plant, its flowers that are bright orange-red in color, its cold hardiness in U.S.D.A. Zone 4, and its ability to be readily propagated by stem cuttings.

2 Drawing Sheets

Botanical classification: *Lychnis×arkwrightii.*
Cultivar designation: 'Pmoore05'.

BACKGROUND OF THE INVENTION

The present invention relates to a new and distinct cultivar of *Lychnis* plant, botanically known as *Lychnis×arkwrightii* 'Pmoore05' and will be referred to hereafter by its cultivar name, 'Pmoore05'. The new cultivar represents a new herbaceous perennial grown for landscape use.

The new cultivar arose from a cross made by the Inventor in 2006 in Stockbridge, United Kingdom between an unnamed and unpatented plant of *Lychnis chalcedonica* as the female parent and an unnamed and unpatented plant of *Lychnis haageana* as the male parent. The Inventor selected 'Pmoore05' as a single unique plant amongst the seedlings that resulted from the above cross in June of 2008.

Asexual propagation of the new cultivar was first accomplished by stem cuttings in Stockbridge, United Kingdom in July of 2008 by the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Pmoore05' as a unique cultivar of *Lychnis.*

1. 'Pmoore05' exhibits a strong growth habit and is quick to produce a marketable plant.
2. 'Pmoore05' exhibits flowers that are bright orange-red in color.
3. 'Pmoore05' is cold hardy in U.S.D.A. Zone 4.
4. 'Pmoore05' is readily propagated by stem cuttings.

The female parent of 'Pmoore05', an unnamed and unpatented plant of *Lychnis chalcedonica*, differs from 'Pmoore05' in having a slower growth habit with slower propagation, flowers that are duller orange in color, in being taller in height, and in having weaker overwintered plants. The male parent of 'Pmoore05', an unnamed and unpatented plant of *Lychnis haageana*, differs from 'Pmoore05' in having flowers that are duller orange in color, foliage lacking a purple tinge, and in being less cold hardy. 'Pmoore05' can be most closely compared to cultivars of *Lychnis×arkwrightii*, 'Vesuvius' (not patented) and 'Orange Gnome' (not patented). 'Vesuvius' differs from in having a less compact plant habit (taller in height), in having flowers that are duller orange in color, and in being slower to propagate by cuttings. 'Orange Gnome' differs from in having a less compact plant habit (taller in height) and in having flowers that are duller orange in color.

BRIEF DESCRIPTION OF THE DRAWING

The accompanying colored photographs illustrate the overall appearance and distinct characteristics of the new *Lychnis*. The photographs were taken of a one year-old plant of 'Pmoore05' as grown in a 5-liter container in IJsselstein, The Netherlands.

The photograph in FIG. 1 is a side view of a plant of 'Pmoore05' in bloom.

Figure 1:
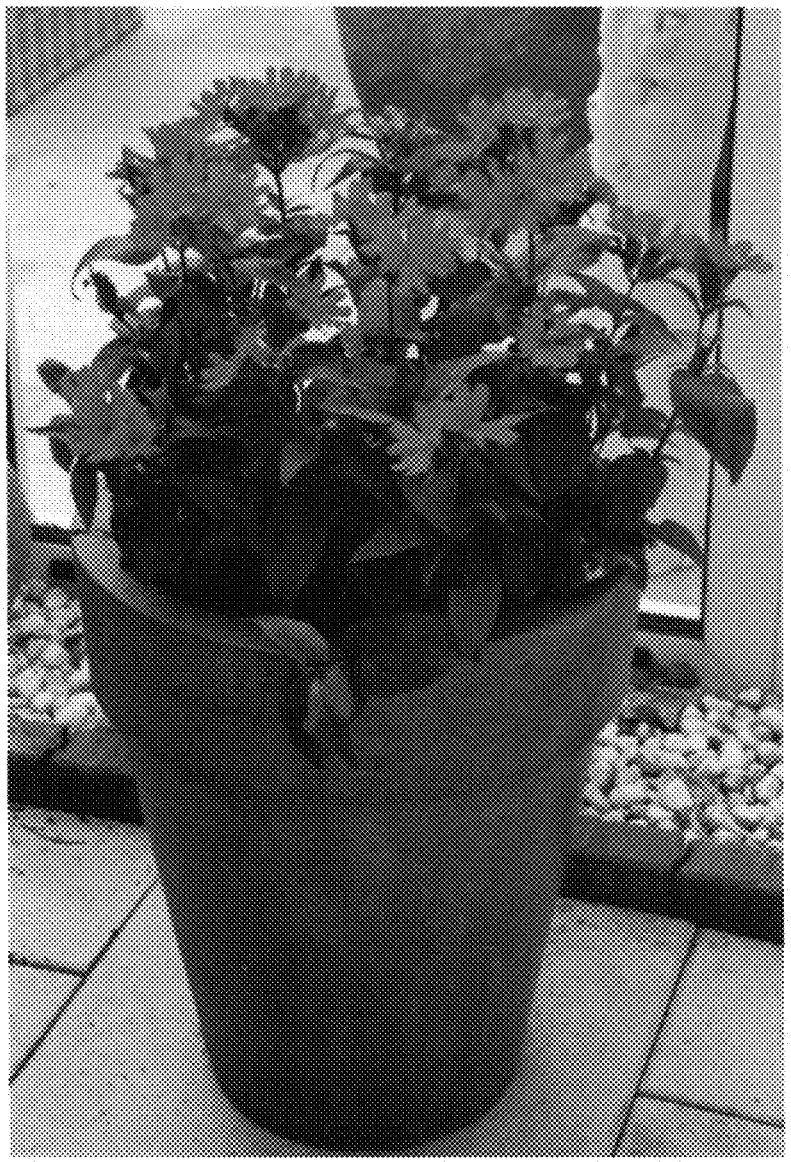
Figure 2:
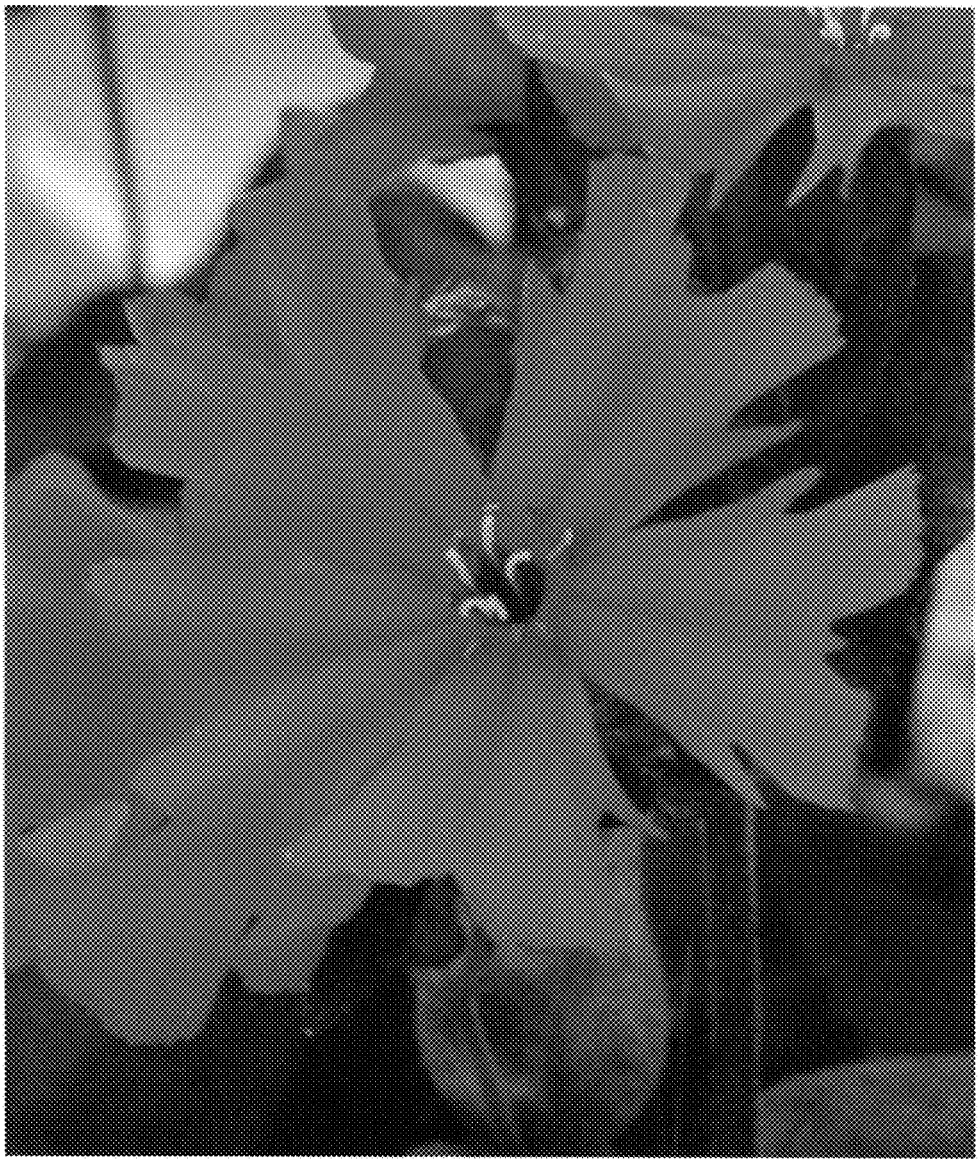

The photograph in FIG. 2 is a close-up view of the flowers of 'Pmoore05'.

The colors in the photograph may differ slightly from the color values cited in the detailed botanical description, which accurately describe the colors of the new *Lychnis.*

DETAILED BOTANICAL DESCRIPTION OF THE PLANT

The following is a detailed description of two year-old plants of 'Pmoore05' as field grown in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

Blooming period: 3 to 4 weeks in mid June in The Netherlands.

Plant habit: Herbaceous perennial, upright.

Height and spread: Reaches about 28.2 cm in height and about 19.8 cm in spread.

Cold hardiness: At least in U.S.D.A. Zone 4.

Diseases and pests: Not more susceptible to pests and disease than other *Lychnis* varieties, *Lychnis* is generally not prone to disease problems.

Root description: Fine, fibrous.

Branching habit: Flowering stems branch freely from the basal foliage.

Growth and propagation:

*Growth rate.*—Vigorous for a *Lychnis* cultivar, grows an average of 8 cm per month in spring.

*Propagation.*—Stem cuttings, fast to propagate by cuttings; a salable plant can be produced from a cutting in about 6 months.

*Root initiation.*—Cuttings initiate roots in about 7 days.

Stem description:

*Stem size.*—Average of 20.7 cm in length and 2.5 mm in diameter.

*Stem shape.*—Round.

*Stem color.*—Young stems; 144B, mature stems; 187A.

*Stem surface.*—Moderately glossy, densely covered in short strigose hairs, 1 mm in length and NN155C in color.

*Internode length.*—An average of 2.9 cm.

*Branching.*—About 6 lateral branches.

Foliage description:

*Leaf shape.*—Ovate.

*Leaf division.*—Simple.

*Leaf base.*—Cuneate.

*Leaf apex.*—Acute to narrow acute.

*Leaf venation.*—Pinnate, not conspicuous, upper side 200B to 200C, lower side 148B.

*Leaf margins.*—Entire, slightly wavy.

*Leaf attachment.*—Sessile.

*Leaf arrangement.*—Opposite.

*Leaf surface.*—Upper surface dull to very slightly glossy, lower surface dull, both surfaces moderately covered with short strigose hairs, 0.75 mm in length and NN155C in color.

*Leaf color.*—Mature upper surface; N137A, mature lower surface; 148B, young upper surface; 146A, young lower surface; 148B, slightly tinged 200C.

*Leaf size.*—Average of 8.1 cm in length and 3.7 cm in width.

*Leaf quantity.*—An average of 14 (7 pairs) per stem.

*Leaf fragrance.*—None.

*Petiole.*—V-shaped, average of 6 mm in width and 3 mm in height, upper side 146C in color, lower side 178A in color.

Flower description:

*Inflorescence type.*—Single flowers at lateral nodes and corymbs on terminal of main stem.

*Lastingness of inflorescence.*—Average of 10 days.

*Inflorescence size.*—An average of 5.3 cm in height and 7.2 cm in diameter.

*Flower fragrance.*—None.

*Flower number.*—Average of 4 per inflorescence, one inflorescence per flowering stem.

*Flower aspect.*—Upright to slightly outward.

*Flower bud.*—An average of 2.4 cm in length and up to 7 mm in width, obovate with short apiculate apex, color is 182B, veined 183B, densely covered with strigose hairs an average of 2 mm in length and 156D in color.

*Flower form.*—Salverform.

*Flower size.*—An average of 4.2 cm in diameter and 3.1 cm in depth.

*Petals.*—5, rotate, upper surface dull and smooth, lower surface velvety, un-fused but free petals are held together by the calyx, spathulate shape, margins have one large tooth on each side, deeply emarginated to lobed apex, 3.7 cm in length and 2.1 cm in width, color when opening upper side; between N30A and 33A, lower part (inside the calyx) 145B, color when opening lower side; 34B to 34C, lower part (inside the calyx) 145B, color when fully open upper side; between N30B and 32A, lower part (inside the calyx) 145B, color when fully open lower side; 34C, lower part (inside the calyx) 145B, petals fading to 44A.

*Calyx.*—Campanulate in form, an average of 2.4 cm in length and 1 cm in diameter.

*Sepals.*—5, rotate, both surfaces dull in appearance and densely covered with strigose hairs, average length 2 mm and 156D in color, oblanceolate in shape, margins are fused into a tubular shape, narrow apiculate apex, base is fused and upper 25% is free, 2.4 cm in length and 4 mm in width, color immature upper side 147C, color immature lower side 182B, veined 183B, color mature upper side 147C, color mature lower side 197A, tip and veins N199B.

*Peduncles.*—An average of 2 cm in length and diameter, strong, average angle of 35° (40° straight upright), puberulent surface and 147B to 147C in color.

*Pedicels.*—An average of 7 mm in length and 1.5 mm in diameter, strong, average angle of 15° (0°=straight upright), puberulent surface and 147B to 147C in color.

Reproductive organs:

*Gynoecium.*—5 pistils, 1.1 cm in length, stigma is club-shaped and curled downward and NN155A in color, style is 1 cm in length and color is NN155A, base 145D, ovary is 144A in color.

*Androcoecium.*—10 stamens, anthers are basifixed and broad ovate in shape, 1 mm in length and 182B in color, filaments are adnate to corolla, 1.4 cm in length, 0.5 mm in width, and 182B in color, pollen is low and 156A in color.

*Seeds and fruit.*—Not observed.

It is claimed:

1. A new and distinct cultivar of *Lychnis* plant named 'Pmoore05' as herein illustrated and described.

* * * * *